United States Patent
Hrycak et al.

(10) Patent No.: US 7,326,280 B2
(45) Date of Patent: Feb. 5, 2008

(54) ENHANCED CARBON DIOXIDE ADSORBENT

(75) Inventors: Michael B. Hrycak, Middletown, DE (US); Douglas B. McKenna, Elkton, MD (US)

(73) Assignee: Micropore, Inc., Newark, DE (US)

( * ) Notice: Subject to any disclaimer, the term of this patent is extended or adjusted under 35 U.S.C. 154(b) by 229 days.

(21) Appl. No.: 11/045,878

(22) Filed: Jan. 28, 2005

(65) Prior Publication Data
US 2005/0160912 A1 Jul. 28, 2005

Related U.S. Application Data

(60) Provisional application No. 60/539,343, filed on Jan. 28, 2004.

(51) Int. Cl.
*B01D 53/02* (2006.01)
(52) U.S. Cl. ............... 96/108; 96/154; 128/205.28
(58) Field of Classification Search ............... 96/108, 96/154; 95/90, 139; 128/203.16, 205.12, 128/205.28; 502/400; 423/230; 252/181.7, 252/192
See application file for complete search history.

(56) References Cited

U.S. PATENT DOCUMENTS

| | | | |
|---|---|---|---|
| 2,395,842 A | 3/1946 | Parry | |
| 2,629,652 A | 2/1953 | Schechter et al. | |
| 3,607,040 A * | 9/1971 | Hervert et al. | 264/109 |
| 4,168,706 A * | 9/1979 | Fletcher et al. | 128/204.16 |
| 4,407,723 A | 10/1983 | MacGregor et al. | |
| 5,165,399 A | 11/1992 | Hochberg | |
| 5,964,221 A * | 10/1999 | McKenna | 128/205.12 |
| 6,699,309 B1 | 3/2004 | Worthington, II | |
| 6,797,043 B2 * | 9/2004 | Nalette et al. | 96/134 |

FOREIGN PATENT DOCUMENTS

EP 0171551 * 2/1986

OTHER PUBLICATIONS

Davis, et al, "The Dependence of the CO2 Removal Efficiency of LiOH on Humidity and Mesh Size", presented by The American Society of Mechanical Engineers, at the Intersociety Conference on Environmental Systems, San Diego, California, Jul. 10-13, 1978.
Davis, et al, "The Factors Influencing the Formation of Li2o3 from LiOH and CO2", presented by The American Society of Mechanical Engineers, at the Intersociety Environmental Systems Conference, San Diego, California, Jul. 14-17, 1980.

(Continued)

*Primary Examiner*—Frank M. Lawrence
(74) *Attorney, Agent, or Firm*—Patton Boggs LLP

(57) ABSTRACT

A CO2 removal system including a member having a first opening and a second opening to enable air flow containing carbon dioxide (CO2) to pass from the first opening to the second opening and lithium hydroxide (LiOH) supported by the member and having an initial water content above an anhydrous level. In one embodiment, LiOH adsorbent density is a maximum of approximately 1.0 g/cm$^3$.

36 Claims, 10 Drawing Sheets

OTHER PUBLICATIONS

Wang, "Residence Time and Carbon Dioxide Scrubbing Efficiency in Life Support Systems", Aviation Space and Environmental Medicine, Feb. 1981.

Military Specification for Lithium Hydroxide (LiOH), Technical, MIL-L-20213E, Naval Sea Systems Command, Jun. 18, 1980.

General Specification NASA-JSC, Requirements for Lithium Hydroxide Used for CO2 Removal in Closed Environments, National Aeronautics and Space Administration, Houston, Texas, Oct. 1994.

"Lithium Hydroxide, Anhydrous", phamplet CAS No. 1310-65-2, FMC Corporation, copyright 2001.

* cited by examiner

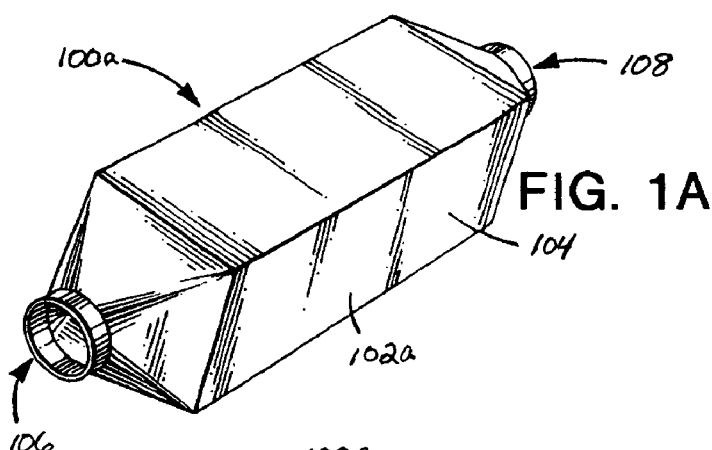
FIG. 1A
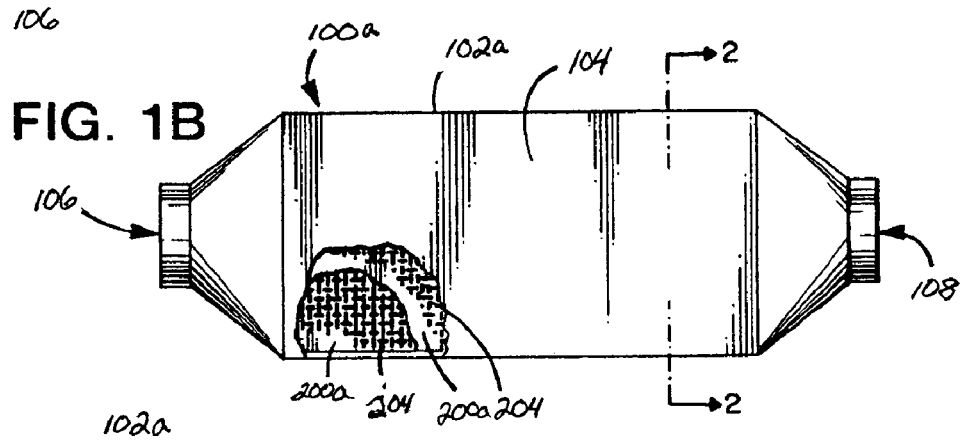
FIG. 1B
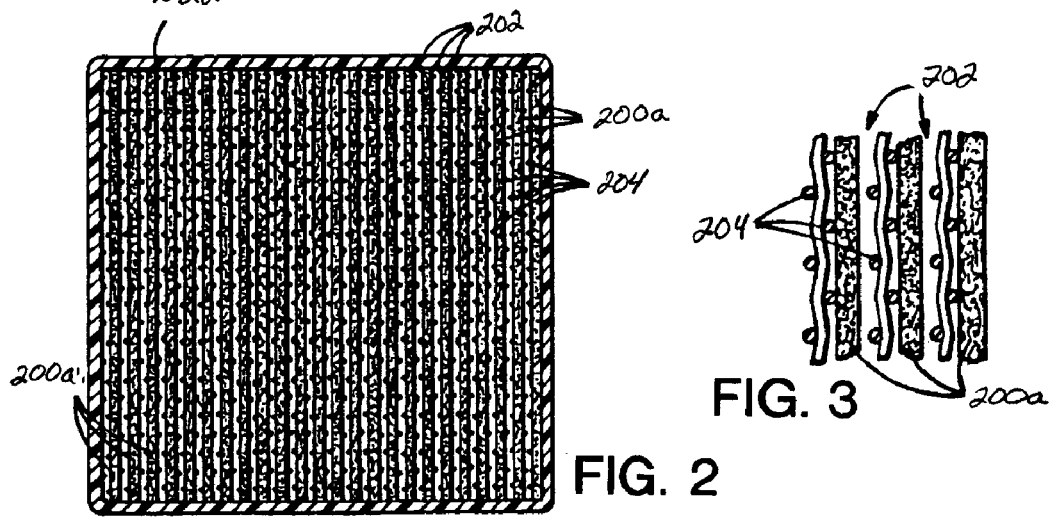
FIG. 2
FIG. 3

ENHANCED CARBON DIOXIDE ADSORBENT

CROSS-REFERENCES TO RELATED APPLICATIONS

This application claims priority from U.S. Provisional Patent Application Ser. No. 60/539,343 filed Jan. 28, 2004, the entire teachings of which are herein incorporated by reference.

BACKGROUND OF THE INVENTION

A rebreather is a device that retains and reuses some or all of a user's expired breath. Even with physical exertion, a person uses only a fraction of the oxygen that is inhaled. A rebreather recirculates unused oxygen in the system and replenishes the oxygen consumed by the wearer. This allows a very small tank of oxygen to last much longer than is possible using traditional self contained breathing apparatus (SCBA) gear. Three main components of typical rebreather systems include a gas supply/oxygen control, counterlung, and carbon dioxide removal system.

The carbon dioxide removal system maintains carbon dioxide $CO_2$ (CO2) pressures at a safe level. Maintaining CO2 at safe pressure levels is relatively easy to do, and is accomplished by passing exhaled gases through a canister filled with a chemical adsorbent, such as soda lime and anhydrous lithium hydroxide (LiOH). Several manufacturers make these adsorbents and use their own special mixes. For example, SODASORB®, manufactured by W. R. Grace & Co., is composed of a mixture of sodium hydroxide, calcium hydroxide, and potassium hydroxide. Granular LiOH adsorbents are typically used in submarine, space, and emergency CO2 removal equipment, where adsorbent volume and weight is maintained at minimal levels.

Adsorbents are typically in the form of small granules that are generally sized between 0.04 to 0.25 inches (1.0 to 6.5 mm) in diameter. The granules may be placed in a canister through which exhaled gases are passed. Smaller granules allow more surface area per unit weight, but because a person must "breathe" through this canister without too much resistance, larger adsorbent particles are employed so as to allow gas flow around these granules and through the canister with a relatively low pressure drop. Thus, one of the limitations of current adsorbent canisters is the relatively large adsorbent particle size necessary to obtain low pressure drops and, in turn, ease of breathing. Additionally, powered or forced air systems typically have low system pressure drop requirements and as a result low adsorbent pressure drops are required. Airflow, gas flow, or the flow of air or gas is defined as the motion of air around an object, not including diffusion. Airflow may be forced air (e.g., via a fan or human respiration) or passive (e.g., thermal convection).

High CO2 removal rates are needed to reduce the size and weight of SCBAs while maintaining acceptable CO2 levels. Once acceptable CO2 levels are exceeded, the adsorbent cartridge is replaced. A 0.5 percent CO2 outlet concentration is typically used to define the replacement point. The CO2 removal capacity can be defined as the total amount of CO2 removed, length of time used (i.e., duration), or both total CO2 removed and duration. Decreasing granule size can increase removal rates (Davis 1978). However, decreasing granule size results in increased pressure drop. System design usually involves trade-off between CO2 removal rate, system pressure drop, CO2 removal capacity, and system size.

LiOH operates to remove CO2 in the following manner. The reaction of CO2 with anhydrous LiOH requires the presence of water (Wang) that, when used in a self-contained breathing apparatus, is provided by exhaled gas in the form of water vapor. The LiOH combines with the water vapor to form lithium hydroxide monohydrate (2LiOH*H2O) and is highly exothermic (i.e., generates heat. The reaction of LiOH and water is described in Eqn. (1):

2LiOH(solid)+2H2O(gas)→2LiOH*H2O(solid), which produces −29.04 kcal/2 moles LiOH of energy.                        Eqn. (1):

The exothermic monohydrate reaction of Eqn. (1) provides heat needed for an endothermic reaction (i.e., absorbs heat) with CO2, and is described in Eqn. (2):

2LiOH*H2O(solid) +CO2(gas)→Li2CO3(solid)+ 3H2O(gas), which absorbs+7.65 kcal/mole CO2 of energy.                        Eqn. (2):

The overall reaction is given in Eqn. (3) and is also exothermic:

2LiOH(solid)+CO2(gas)→Li2CO3(solid)+H2O(gas), which produces −21.39 kcal/mole CO2 of energy.                        Eqn. (3):

Because the LiOH is anhydrous (i.e., substantially without water), the initial source of the water that is needed for the reaction with CO2 is water vapor in an incoming gas stream. The source of the water vapor in the incoming gas stream includes ambient water vapor (i.e., ambient humidity) and/or vapor from human respiration. Davis showed that the CO2 removal efficiency of anhydrous LiOH granules falls rapidly under dry conditions.

Although water is needed for the reaction between LiOH and CO2, too much water vapor has been shown to be detrimental to the reaction. The CO2 removal efficiency of anhydrous LiOH granules improves as humidity is increased up to an optimum humidity level (Davis 1978). Above this level, the CO2 removal efficiency decreases. The presence of an optimum humidity level indicates that there is an optimum operating water content for LiOH granules.

While anhydrous LiOH requires hydration to have a CO2 reaction, the use of pre-hydrated porous LiOH granules (i.e., LiOH granules having an initial water content above an anhydrous level) has also been studied by Davis (1980). In this study, it was concluded that there is not a significant difference in the reactivity between wet and anhydrous LiOH granules. Without a CO2 removal benefit, pre-hydration of granules only increases the weight of the adsorbent, which is not desirable. Wang demonstrated that the CO2 adsorption capacity was generally lower by approximately 10 percent for partially hydrated (e.g., 5.45 percent water-by-weight) LiOH granules. These studies indicate that the pre-hydration of LiOH granules provides no benefit and may be even detrimental for CO2 removal and adsorbent weight.

In summary, although water is important for the CO2 removal reaction, Wang, Davis and others have shown that only water in vapor form is beneficial and too much water, even in vapor form, is detrimental to the reaction of LiOH and CO2. Pre-hydration of the LiOH has been shown to be ineffective at best and detrimental at worst.

As indicated in Eqn. 1, the addition of water to anhydrous LiOH results in an exothermic reaction, which generates heat. Additionally, the overall reaction in the reaction as described in Eqn. (3) shows heat generation. Because the heat given off in the reaction described in Eqn. (1) is 3.8 times as high as the heat absorbed in the reaction described in equation (2), the generation of heat is dominated by the reaction of LiOH with water. The main driving force for the rate of heat generation is the rate at which LiOH reacts with water. In general, the use of LiOH for CO2 removal operates effectively for removing large amounts of CO2, but drops off relatively quickly after an initial reaction (see FIG. 19, between points A and B).

The main driving force for the total amount of heat generated is the total amount of LiOH reacted with water. In closed systems, such as submarine CO2 removal systems, the heat generated can result in adsorbent exhaust temperatures as high as 160 degrees Fahrenheit. Adsorbent surface temperatures are even higher. This level of heat generation results in excessive breathing temperatures for closed systems, such as a rescue hood used by firefighters, is detrimental in most applications. One technique for reducing adsorbent system exhaust temperature includes utilizing molecular sieves downstream of CO2 removal systems, but are problematic due to added weight, size, cost, and breathing resistance.

SUMMARY OF THE INVENTION

The principles of the present invention provide for carbon dioxide adsorbent compounds composed of lithium hydroxide adsorbent that has an initial water content above an anhydrous level. The pre-hydrated carbon dioxide adsorbent or compound provides for higher rates of removal of CO2 over longer periods of time and produces lower temperatures. The pre-hydrated carbon dioxide adsorbent compound reacts opposite to previous studies which show pre-hydrated LiOH granules performing the same or worse than anhydrous LiOH granules. One reason for the differing and unexpected results is the LiOH adsorbent density. In one embodiment, the LiOH adsorbent density is at or below 1.0 g/cm$^3$.

In one embodiment, the principles of the present invention include a CO2 removal system including a member having a first opening and a second opening to enable air flow and containing lithium hydroxide (LiOH) supported by the member and having an initial water content above an anhydrous level. In one embodiment, LiOH adsorbent density is a maximum of approximately 1.0 g/cm$^3$.

In another embodiment, a method for removing carbon dioxide may be performed by including pre-hydrated LiOH adsorbent in a location having airflow with carbon dioxide. The carbon dioxide is removed with the pre-hydrated LiOH adsorbent.

BRIEF DESCRIPTION OF THE DRAWINGS

A more complete understanding of the method and apparatus of the present invention may be obtained by reference to the following Detailed Description when taken in conjunction with the accompanying Drawings wherein:

FIG. 1A is a perspective view of square shaped gas adsorption canister of the present invention;

FIG. 1B is a side view of the embodiment of FIG. 1A;

FIG. 2 is a cross-section view of parallel aligned sheets taken along line 2-2 of FIG. 1B;

FIG. 3 is an enlargement of a portion of the cross-section shown in FIG. 2.;

DETAILED DESCRIPTION OF THE DRAWINGS

Figure 4:
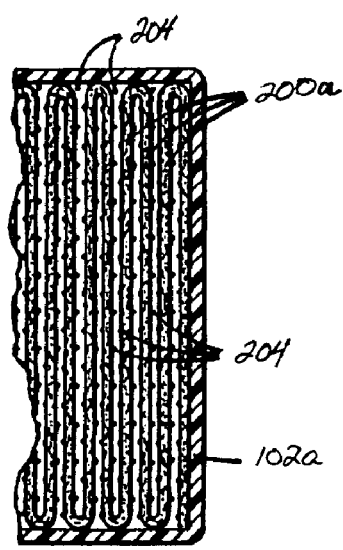
FIG. 4 is a cross-section view of a canister of the present invention having a pleated sheet.

LiOH may be processed to produce a number of different anhydrous forms for use in carbon dioxide removal systems used in rebreather systems. The different forms of anhydrous LiOH include anhydrous powder and granules. The powder and granules may be utilized to form a number of different products for use in carbon dioxide removal systems, including powder packed in gas permeable enclosures, granules packed in gas permeable enclosures, and sheets formed of powder, for example. The gas permeable enclosures and sheets may be waterproof for water applications, such as SCUBA systems.

According to the principles of the present invention, and contrary to conventional LiOH studies, CO2 removal may be improved over longer periods of time by (i) utilizing anhydrous LiOH products that have lower densities than conventionally utilized and (ii) pre-hydrating the anhydrous LiOH products. Additionally, the principles of the present invention provides for reduction in heat generation.

Anhydrous LiOH describes LiOH with substantially no water content. In one composition, porous anhydrous LiOH powder has properties of 99.0 percent LiOH and 0.6 percent Li2CO3. This sets the level of the remaining impurities (H2O, CaO, etc) to 0.4 percent. Thus, the water content of porous anhydrous LiOH powder is a maximum of 0.4 percent. Military and other specifications limit the amount of initial water content of the LiOH that may be used for certain applications and/or systems. For example, MIL-L-20213E (SH), Military Specification, Lithium Hydroxide (LiOH), Technical Section 3.8.2 Moisture Content, where it is stated that the moisture content (of granular LiOH used in Navy submarines) shall not exceed 0.50 percent by weight. SD-L-0024B, General Specification, NASA-JSC Requirements for Lithium Hydroxide Used for CO2 Removal in Closed Environments, Section 3.5.2 Moisture Content, where it is stated that the amount of H2O in a lot sample (of granular LiOH used in spacecraft, space stations, spacesuits, emergency rebreathers, and other closed loop air systems used in space) shall not exceed 1.0 percent by weight. Anhydrous LiOH, therefore, has substantially no water other than that which remains after the manufacturing process to produce the anhydrous LiOH, as understood in the art. While the specific anhydrous levels of the LiOH may vary depending on the manufacturing process composition, and form, the percentage of water of anhydrous LiOH is a low percentage, as understood in the art.

Density of LiOH Adsorbent

LiOH adsorbent is defined as any adsorbent containing LiOH with a minimum dimension of 0.04 inches. This minimum dimension can be described as the minimum distance between two parallel plates that the adsorbent can fit through.

LiOH adsorbent can be in many forms, the most familiar of which is granular. Granules come in many shapes, including but not limited to spherical, semi-spherical, prism, cylindrical, semi-cylindrical and random, etc. Other LiOH adsorbent shapes include, but are not limited to, that described in the McKenna (U.S. Pat. No. 5,964,221) and Hochberg (U.S. Pat. No. 5,165,399), which are incorporated herein by reference and which can be largely described as LiOH in sheet form. In sheet form, the minimum dimension corresponds to the total thickness of the sheet that may or may not include a separating means to provide airflow between. Other forms include, but are not limited to, extruded forms where gas flow channels are molded directly into the adsorbent.

The LiOH adsorbent density (i.e., density of LiOH adsorbent), is the mass of the LiOH adsorbent divided by the volume of the LiOH adsorbent. The volume of the LiOH adsorbent does not include the volume of the gas flow channels around the LiOH adsorbent. Likewise, the mass of LiOH adsorbent does not include non-LiOH components. Additionally, the density calculation is made using the mass of anhydrous LiOH adsorbent. As such, if the LiOH adsorbent contains water in the form of LiOH monohydrate, then the LiOH adsorbent mass is determined by subtracting the water weight prior to calculating density.

The LiOH adsorbent density of the different LiOH adsorbent forms, results from the process by which they are made. For example, the process to make porous anhydrous lithium hydroxide granules uses lithium hydroxide monohydrate (see, for example, U.S. Pat. No. 2,629,652). Crystalline lithium hydroxide monohydrate is pressed into a cake at high pressure. The cake is then crushed into granules to the desired size and the fine granules are screened out. The resulting granules are heated until reaching an anhydrous condition with the loss of water creating the pore structure of the granule. The porosity of the granule increases surface area and provides pathways for the diffusion of CO2 and water vapor into the internal structure of the granule. Other conventional methods for making porous anhydrous LiOH granules include the direct formation of LiOH granules and then drying to create an anhydrous condition. The LiOH adsorbent density of the porous anhydrous LiOH granule is 1.0 g/cm$^3$.

Products with Anhydrous LiOH

The principles of the present invention provide a gas adsorbent system containing anhydrous and monohydrate LiOH combined with a LiOH adsorbent density lower than 1.0 g/cm$^3$ that improves CO2 absorption rate, amount of CO2 absorbed and reduces reaction temperature. Because the principles of the present invention provide for more efficient and longer lasting CO2 removal, the CO2 filter may be smaller than conventional CO2 filters.

As the mechanism for removing CO2 from a gas is dependent on the particular material chosen, the use of the word "adsorption" in this specification is meant to include adsorption, absorption, chemisorption, and so forth. In FIGS. 1A and 1B, an improved gas adsorbent canister device, indicated generally at 100a, comprises wall 102a defining a hollow canister body 104 that has a gas inlet 106 and outlet 108. The canister 100a can be of any shape, such as rectangular or cylindrical. The canister 100a may be composed of a rigid material, such as glass fiber reinforced plastic. As is illustrated in FIGS. 2 and 3, the inside hollow portion of the canister 100a contains porous, air permeable sheets 200a, which are optionally water resistant and contain an adsorbent material. These sheets 200a may be aligned parallel to the direction of gas flow and run substantially the length of the canister 100a. Expired gases pass through the inlet 106 of the gas adsorption canister 100a, through the space 202 or separating screens 204 between the sheets 200a, and out though the outlet 108. As expired gases flow past these adsorbent sheets 200a, certain gases diffuse into the sheets 200a and react with or are adsorbed by adsorbents (e.g., LiOH) contained therein. Since the sheets are aligned parallel to the gas flow, a controlled and lower pressure drop is maintained, as well as uniform flow past the sheets 200a, thereby allowing for efficient adsorption and a uniform depletion of the adsorbent contained in the sheets 200a.

As shown in FIG. 2, the canister 100a contains a plurality of gas-permeable adsorbent sheets 200a, which is optionally porous hydrophobic. The sheets 200a may be aligned so that the gas flows substantially parallel to the sheets 200a. In this embodiment, the canister body 104 has a rectangular cross-section. The sheets 200a are spaced apart from each other by separating screens 204. FIG. 3 depicts the adsorbent sheets 200a and separating screens 204 where the separating screens 204 are positioned between the sheets 200a.

The separating screen 204 and sheets 200a are held in position parallel to the gas flow through the canister. The separating screen 204 and sheets 200a may be directly attached to the canister wall 102a, indirectly attached by use of a frame or other device that is attached to the canister wall 102a, or held in place by the internal shape of the canister 100a.

FIG. 4 shows another embodiment taken along line 2-2 of FIG. 1B, where a rectangular canister body 104 contains a sheet 200a that is "pleated" and portions of the pleated sheet are spaced apart by separating screens 204. The separating screens 204 need not be attached to the canister body 104 or to the sheet 200a.

Figure 5:
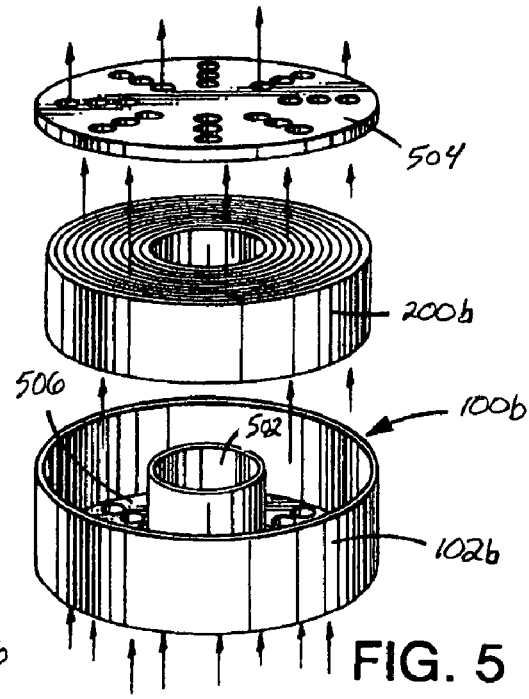
FIG. 5 is a three-quarter perspective view of an adsorption canister of the present invention where the canister is cylindrical and the sheets are spiral.
Figure 6:
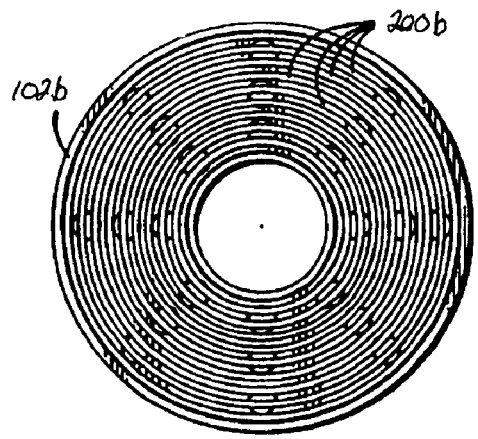
FIG. 6 is a cross-section top view of the adsorption canister of FIG. 5 where the sheets inside the canister have a spiral configuration.
Figure 7:
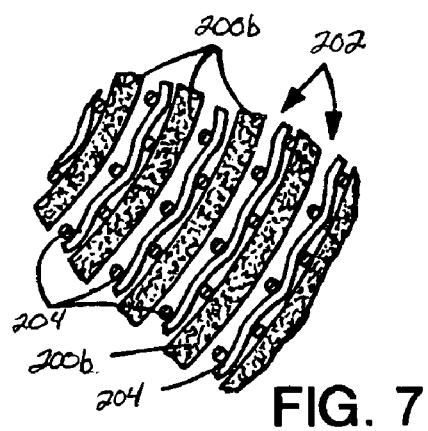
FIG. 7 is an enlargement of the circular area of the cross-section shown in FIG. 6 showing the sheets separated by a separating means.

As illustrated in FIG. 5, in another embodiment, the canister 100b may have a circular or cylindrical shape. The canister 100b may have an opening 502 in the middle giving the canister 100b a donut shape or the canister 100b may be solid. In the embodiment depicted, the sheets 200b are spiraled (i.e., arranged in a continuous helix or as separate rings or helixes arranged concentricity). Airflow through the cylindrical canister 102b is from bottom to top as indicated on FIG. 5 and is parallel to the spiraled adsorbent sheet surfaces. Airflow is through end plates 504 and 506. FIG. 6 shows a top view of cylindrical canister 102b of FIG. 5 with adsorbent sheet 200b arranged within the canister 102b in the "spiral" configuration where the sheet is wrapped around the center. FIG. 7 shows separating screens 204 positioned between the spirally positioned sheets 200b.

The flow rate of expired gas through the canister is controlled by the total space between the adsorbent sheets. Accordingly, a canister with a larger cross-sectional area, or a thicker separating means, would have the effect of reducing the velocity of gas flow past the adsorbent sheets. This velocity must be matched with the length of the canister to achieve the desired adsorption rate for a particular application and adsorbent material. Whether configured as LiOH sheets or granules, the LiOH is supported by the canister. If no canister is used (i.e., cartridges only), then the LiOH is considered to be supported by the cartridge.

The principles of the present invention also provide a gas adsorbent sheet 200a that provides isolation of the adsorbent from the user in wet and dry environments. The sheets 200a are constructed to contain adsorbent particles within and to withstand exposure to vibration, air, and water without releasing the adsorbent particles. Various embodiments of sheets 200a are shown in FIGS. 8, 9, 10, 11, and 17A-17E, and are described below.

Figures 8, 9, 10, 11:
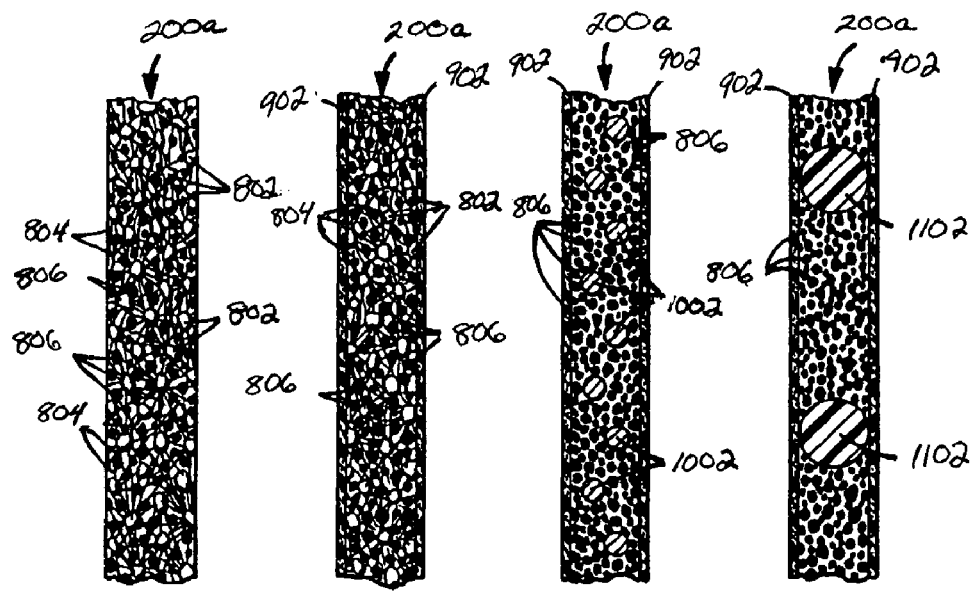
FIG. 8 is a cross-section view of an adsorption sheet of the present invention where the sheet is formed of expanded polytetrafluoroethylene with adsorbent particles encapsulated within.
FIG. 9 is a cross-section view of an adsorption sheet of the present invention where the sheet of FIG. 8 is surrounded by an outer membrane.
FIG. 10 is a cross-section view of an adsorption sheet of the present invention where adsorbent material is attached to an internal screen and outer membranes are attached to the adsorbent particles.
FIG. 11 is a cross-section view of an adsorption sheet of the present invention where outer membranes are attached to an internal screen and the interstices in the screen contain adsorbent material.

In one embodiment shown in FIG. 8, sheet 200a is formed of an adsorbent filled expanded porous PTFE sheet having a microstructure of nodes 802 interconnected with fibrils 804, wherein LiOH particles 806 is present in the voids of the PTFE structure as taught by U.S. Pat. No. 4,985,296 issued to Mortimer, Jr., which is incorporated herein by reference. This sheet 200a may be water repellent and/or air-permeable. Ideally, LiOH particles 806 are packed in a multi-modal (e.g., bi-modal or tri-modal) manner, with particles of different sizes interspersed around one another to fill as much of the available void space between particles as is possible so as to maximize the amount of active material contained in the sheet 200a. This technique also allows more than one type of adsorbent particle to be filled into a single sheet.

By using filled porous expanded polytetrafluoroethylene (ePTFE) in the sheet 200a, a number of additional features may be further imparted. Expanded PTFE is a non-linting, non-out-gassing inert material that effectively reduces dusting of adsorbent material during manufacturing and during the life of the CO2 filter. Additionally, processing of this material includes the ability to make a relatively thin material that can be produced in a wide sheet and then cut (or cut and pleated) into desired configurations.

The properties of CO2 adsorbent filled ePTFE sheets are such that no other supporting fabric or material is needed to maintain structural integrity. In fact, not only can this filled ePTFE sheet withstand flexing, pleating and mechanical vibration under dry conditions, the hydrophobicity of the ePTFE offers this structural durability even while subjected to direct liquid water contact, without water ever mixing with the CO2 adsorbent. Thus, this embodiment of sheet 200a is ideal for preventing the "caustic cocktail" problem.

Another embodiment of the sheet 200a is shown in FIG. 9, where the filled ePTFE sheet 200a is encapsulated between two gas-permeable membranes 902. In one embodiment, the gas permeable membranes are hydrophobic. These outer membranes 902 add extra protection to ensure that the adsorption material 802 is contained within the sheet 200a while preventing water from reaching the adsorbent contained in the sheet. The membranes 902 have a high degree of filtration efficiency to prevent adsorbent particles from escaping into the breathing gas circuit. These membranes 902 may be composed of porous expanded polytetrafluoroethylene (ePTFE), which are hydrophobic and offer high particulate filtration efficiency. Additionally, PTFE may be able to be formed in extremely thin dimensions while remaining coherent and pin-hole free, and may be able to be made into wide widths that can be slit or cut to the desired width. The thinner the membrane the greater the filter adsorption rate in a given volume. As such, these outer membranes 902 may be very thin and need not be used to add any structural integrity but merely to provide filtration and hydrophobicity only. The outer membranes 902 can be attached to the sheet 200a by a thermoplastic adhesive polymer. With the additional protection of these outer layers of ePTFE, the use of more effective but potentially more hazardous CO2 adsorbents is contemplated.

A third embodiment of the sheet is shown in cut-away FIG. 10 where an internal screen 1002 is encapsulated by adsorbent material 806 that may be surrounded by two hydrophobic gas-permeable membranes 902.

A fourth embodiment of the sheet 200a is shown in FIG. 11 where an internal screen 1102 is attached to two hydrophobic gas-permeable membranes 902 and the adsorbent material 806 is positioned in the voids between members of the internal screen 1102.

Figures 12, 13, 14:
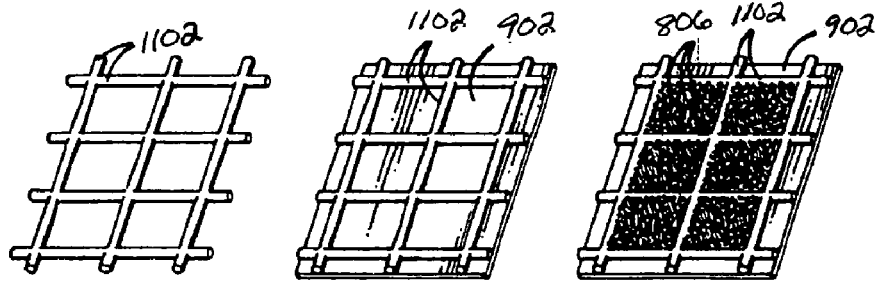
FIGS. 12 through 15 are three-quarter elevation views of a method for forming the sheet of FIG. 11.

FIGS. 12 thorough 15 illustrate a method for making the sheet 200a of FIG. 11 having an internal screen 1102, adsorbent material 802, and outer membranes 902. FIG. 12 depicts the internal screen 1102. Next, in FIG. 13, internal screen 1102 is attached to a membrane 902 by a lamination process. Subsequently, in FIG. 14, adsorbent material 806 is added into the open cells of internal screen 1102. Afterwards, in FIG. 15, a second membrane 902 is laminated to the top of the internal screen 1102, thereby encapsulating the adsorbent material 802 within.

Figures 15, 16:
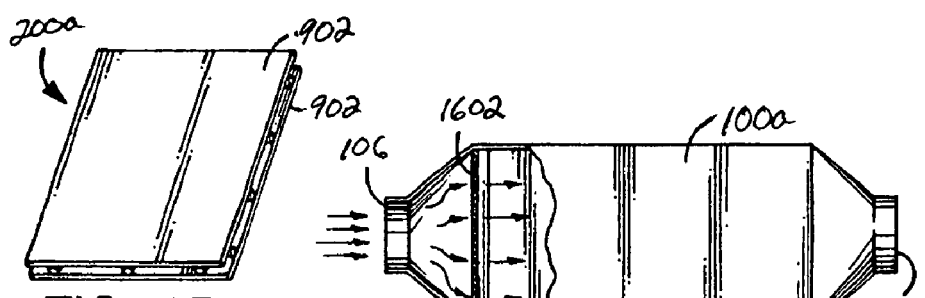
FIG. 16 is a cut-away view of the canister of FIG. 1 and depicts a diffusion panel that redistributes gas flow equally across the canister cross section.
Figure 17A:
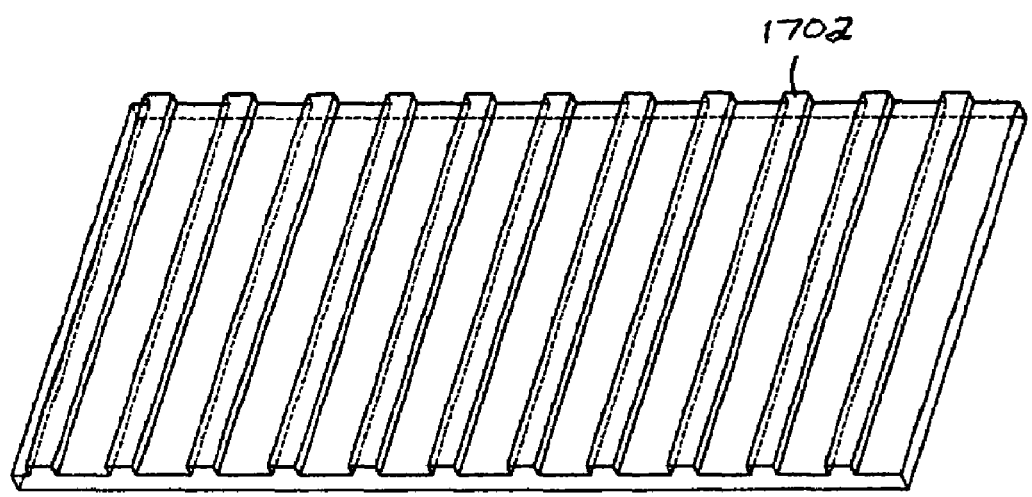
FIGS. 17A through 17E are illustrations of various embodiments of a molded structure of LiOH sheets.
Figure 17B:
Figure 17C:
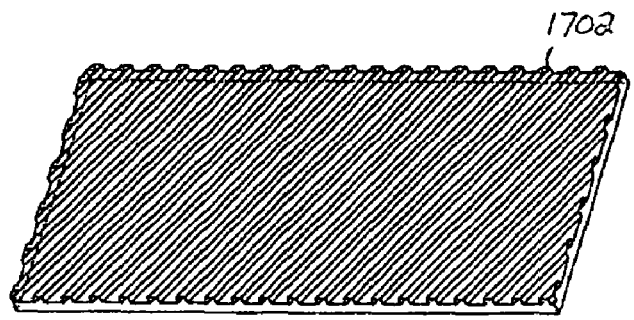
Figure 17D:
Figure 17E:
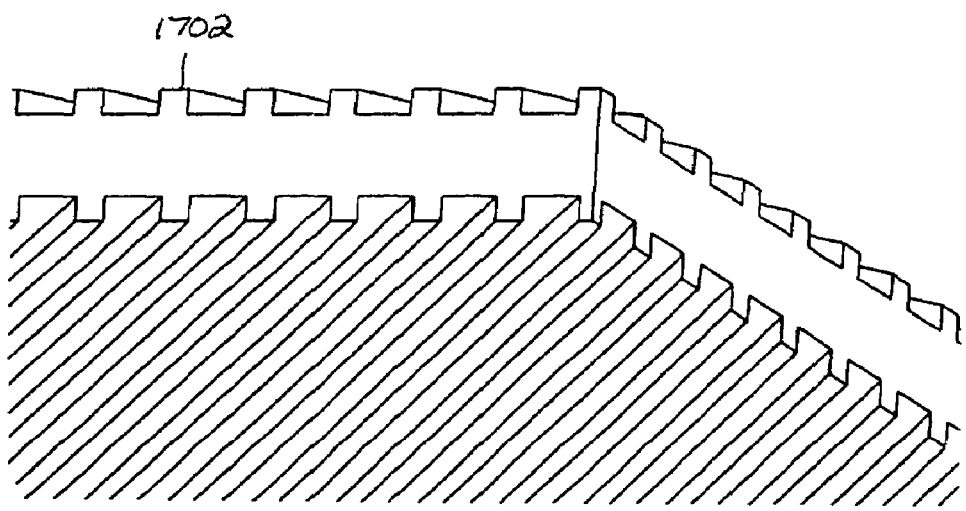

In another embodiment as shown in FIG. 16, a gas diffusion panel 1602 is placed upstream of adsorbent sheets 200a. The diffusion panel 1602 acts to redistribute the gases flowing through the canister 100a such that gases flow evenly between the adsorbent sheets 200a. This redistribution of gas occurs because of the pressure drop across the diffusion panel 1602.

The diffusion panel 1602 may be composed of a flat sheet that can be made out of any porous material such as sintered plastics or metals, woven and non-woven synthetic or natural fabrics, and the like. The gas diffusion panel 1602 is preferably not hydrophobic to the extent that if water enters the canister 100a, it will be able to flow through the diffusion panel without building up any significant pressure. Through the use of this diffusion panel, the amount of gas flowing past each individual sheet 200a is largely determined by the uniformity of the diffusion panel 1602. This, in addition to the precise sheet 200a spacing via separating screens 204 with uniform thickness, allows for excellent uniformity in flow, and in turn, adsorbent reaction, and utilization of the internal dimensions of the canister 100a.

LiOH Sheet Structure

Various embodiments of a molded structure of LiOH sheets are illustrated in FIGS. 17A through 17E. By molding the separating elements 1702 (or "ribs") directly out of adsorbent material, not only is the adsorbent cartridge easier to produce, but, because of its self-separating properties, the total amount of adsorbent in the filter can be increased by 10 to 30 percent.

Molding the separating elements 1702 also assists in controlling the height to width ratio of the rib itself. Because the amount of adsorbent material contained in the molded separating ribs adds significantly to the total capacity of the adsorbent system, it is desirable to also optimize the rate at which adsorbent is depleted in the rib. If the environmental conditions in which the canister operates is thermally constrained, it is desirable to have a smaller surface area to volume ratio, and as such, a width to height ratio of the rib of greater than two to one (2:1) is desirable. If the environmental conditions of operation cause the adsorbent system to be diffusion constrained, the rib width can be made at about the same thickness of the adsorbent sheet itself. It is also possible depending on test conditions, to use the adsorbent contained in the rib area to change the shape of the CO2 outlet concentration versus time curve.

LiOH Sheet Forming Process

Figure 18A:
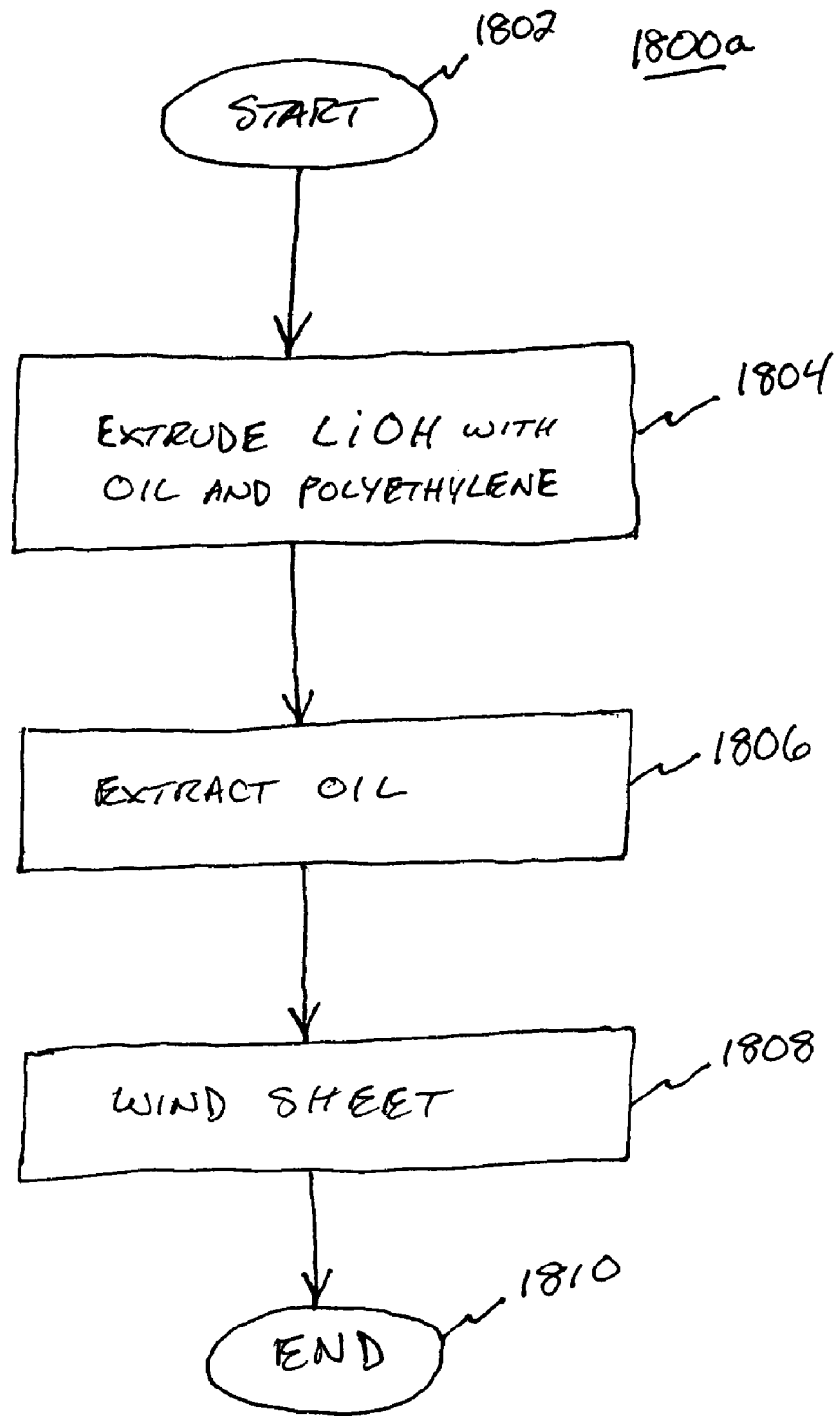
FIG. 18A is a flow chart of an exemplary process for producing a sheet of anhydrous LiOH includes extrusion, extraction, and winding.

FIG. 18A is a flow chart of an exemplary process 1800a for producing a sheet of anhydrous LiOH that includes extrusion, extraction, and winding. The process starts at step 1802. At step 1804, the extrusion process may be performed by mixing mineral oil, polyethylene powder and anhydrous lithium hydroxide in an extruder, such as a Mega 50 Compounding Machine operating at a temperature of 170C. to form an extruded LiOH compound. A heated die may be used to extrude the material into a flat sheet. The extruded LiOH compound may be pinched between a smooth calendar roll and a calendar roll with grooves. The calendar roll with grooves imparts protrusions, such as a permanent rib structure, into the sheet, thereby forming the basis for flow channels in a cartridge. The ribbed sheet may be cooled below the polyethylene melt point and then wound into a roll. One exemplary extruded composition is 65.3 percent LiOH, 33 percent oil, and 1.7 percent polyethylene, weight/weight percentage. EXAMPLES 1 and 2 hereinafter describe exemplary rib spacing and dimensions, and base sheet thickness. The separation distance between the calendar rolls controls the base sheet thickness. The groove dimensions and spacing of the calendar rolls control the rib dimensions and spacing.

At step 1806, an extraction process may be used to remove the oil in the rolls using a solvent, such as hexane, to perform a liquid-to-liquid extraction. During the oil extraction process, the rolls are saturated with liquid hexane. The rolls are heated to 250 degrees Fahrenheit and vacuum dried until the hexane is removed. The rolls are cooled to ambient temperature and stored in a CO2 free environment.

At step 1808, a winding process may include a winder used to wind the sheet into a cartridge. In one embodiment, the winder includes a slitter for sizing the wound sheet into a desired cartridge length. At this point, the cartridge is considered to be a sheet composed of anhydrous LiOH that may be included in a rebreather or scrubber system and used for removal of CO2 in gas.

The sheet may be wound onto a polyethylene core. A thermoplastic film is attached to the core and the sheet is pinched between the film and core in order to begin the winding of a cartridge. Winding is stopped when a desired cartridge diameter is reached. An end of the cartridge may be terminated by (i) inserting the thermoplastic film between the two outer layers of sheet, (ii) winding the film around onto itself, and (iii) attaching the film to itself. The process ends at step 1810.

Since the reaction chemistry is the same for the cartridge of LiOH and porous anhydrous LiOH granules, similar heat generation and temperature effects can be observed during CO2 removal.

Additional forms of CO2 adsorbent systems include rectangular cartridges, vertically suspended sheets (with or without protective covering) and covered panels of sheets within a hood. Additional forms of adsorbent material include the use of PTFE instead of PE. Porous waterproof PTFE membranes on the adsorbent surface may also be utilized.

Another embodiment for producing LiOH sheets includes producing granules from the extrusion process. The extrusion process includes mixing mineral oil, polyethylene powder, and anhydrous LiOH in an extruder. The material is processed into an injection-molding machine and formed into granular shapes. The shapes can be any geometric shape, such as spherical, hemispherical, cylindrical, hemi-cylindrical, prism. Random shapes may be made by breaking up a sheet or block of cleaned material into the desired size. The size of the granule is determined by the pressure drop, CO2 removal rate, system volume and CO2 removal capacity requirements of the application. The granules are cooled below the polyethylene melt point and then collected into a screening tray. An exemplary extruded composition may be 65.3 percent of LiOH, 33 percent of oil, and 1.7 percent polyethylene, weight/weight percentage.

The extraction process removes the oil in the granules by using hexane to cause a liquid-to-liquid extraction. During the oil extraction process, the granules become saturated with liquid hexane. The granules are heated to 250 degrees Fahrenheit and vacuum dried until the hexane is removed. The granules are cooled to ambient temperature and stored in a CO2 free environment.

Although previous studies of pre-hydrating porous anhydrous LiOH granules showed no or a negative performance benefit, pre-hydration of LiOH adsorbent having lower LiOH adsorbent density was attempted resulting in improved CO2 removal performance. While the principles of the present invention employs LiOH adsorbent that is pre-hydrated, LiOH adsorbent density affects the CO2 removal performance of the LiOH adsorbent. Generally speaking, pre-hydrated LiOH is anhydrous LiOH, in any form, that has been re-hydrated above an anhydrous level prior to use. The pore structure and total pore volume of the porous anhydrous LiOH granule results directly from removal of water from LiOH*H2O. The LiOH adsorbent density of the porous anhydrous LiOH granule is 1.0 g/cm$^3$. At this density, pre-hydration of the LiOH granule does not improve performance. However, the LiOH in other forms, such as sheets, have pore structures inside LiOH particles plus a void space between particles, inside the sheet. This void space between LiOH particles within the adsorbent sheet, results in a lower LiOH adsorbent density than that of granules. The loss of LiOH mass due to a lower LiOH adsorbent density is more than made up by the gain in density obtained from efficient packing of LiOH into a cartridge (e.g., a rolled sheet). The lower densities of the porous anhydrous LiOH enables the pre-hydration process of the LiOH to have improved CO2 removal performance.

Hydration of LiOH granules with lower LiOH adsorbent densities than 1.0 g/cm$^3$ are performed by placing the LiOH granules on a conveyor belt and spraying the LiOH granules with water. The spray system may include an ultrasonic spray head that distributes a fine mist of water across the width of the material. A water lay-down flow is held constant and a line speed controller controls the conveyor belt velocity. The conveyor belt velocity is determined by a combination of the starting moisture content, the target moisture content, the conveyor belt granule density in mass/area, and the water lay-down flow. The conveyor belt may be vibrated in order to expose unsprayed surfaces and multiple sprays used to more evenly coat the exterior surfaces of the LiOH granules with water. The LiOH granules are allowed to cool in a CO2 free environment before packaging.

Figure 18B:
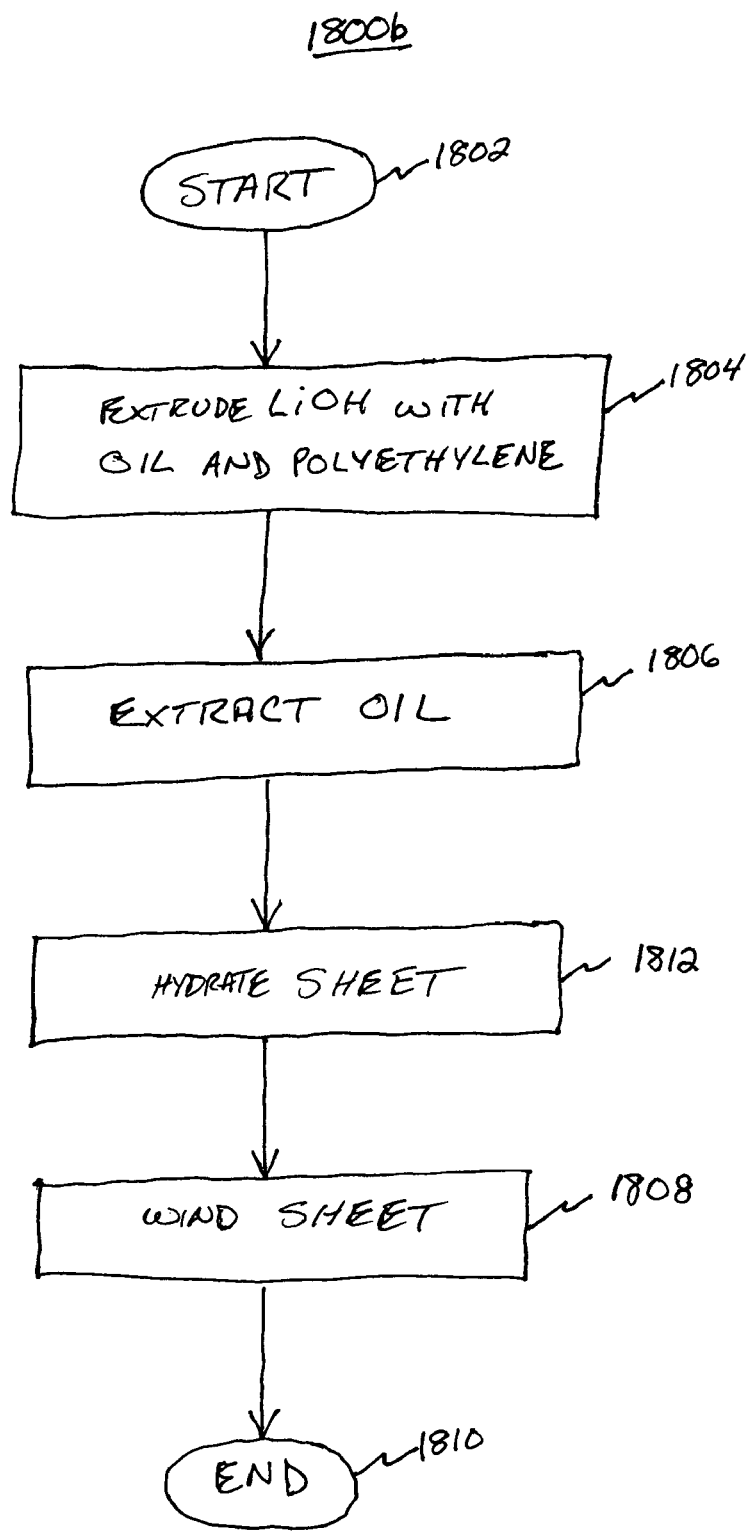
FIG. 18B is a flow chart of an exemplary process for producing a sheet of anhydrous LiOH that includes hydrating the sheet of anhydrous LiOH.

FIG. 18B is a flow chart of an exemplary process for producing a sheet of anhydrous LiOH that includes hydrating the sheet of anhydrous LiOH. Steps 1802, 1804, 1806, and 1808 describe processing steps to produce anhydrous LiOH sheets and may be the same or similar to those described in FIG. 18A. At step 1812, the anhydrous LiOH sheet may be hydrated. The hydration may be performed by a variety of hydration techniques. In one embodiment, a winder may include an optional spray system for delivery of water and a take up system that rolls the hydrated sheet into a cartridge. The spray system may include an ultrasonic spray head that distributes a fine mist of water across the width of the roll. Water lay-down flow may be held constant and a line speed controller controls the sheet velocity. The sheet velocity may be determined by a number of different parameters, such as starting moisture content, target moisture content, sheet weight in mass/area, and water lay-down flow.

For a ribbed sheet of CO2 adsorbent, hydration may occur before the sheet is wound into a cartridge. Hydration is typically done by the uniform addition of liquid water to the surface of the ribbed side (facing upward) of the sheet. Rolling the sheet up allows water to contact and penetrate into the sheet from two directions: into the ribbed side and into the structureless or smooth side. The ribs form channels that retain the water and prevent the water from being squeezed out when the sheet is rolled up onto a core. Alternatively, water may be applied to the smooth side of the sheet. Water may be evenly applied by the use of an ultrasonic spray mister or by the use of water spray nozzles, for example. The amount of water deposited is controlled by the total water flow to the spray system and the rate at which the sheet is passed below the spray system.

Hydration may also be performed by the addition of water vapor using a CO2 free gas stream. A CO2 free nitrogen gas can be humidified by using mists or bubbling through a heated water bath. Monitoring the weight gain of the sheet and removing the sheet when the desired hydration level is achieved provides a control of the amount of hydration. In order to reduce nitrogen costs, several batches of sheet can be put in series and/or the nitrogen gas recirculated.

The final hydration level can be more precisely achieved by measuring the moisture content of the sheet before hydration, which is typically below about one percent. To measure the moisture content, a moisture balance may be utilized. Non-sheet forms of the adsorbent can be hydrated by using variations of the methods described above.

After spraying, the sprayed material is allowed to cool to ambient temperature in a CO2 free environment. In handling the hydrated LiOH during this time period (e.g., approximately 30 minutes or less), the sprayed LiOH compound is positioned such that the water is allowed to hydrate the compound. The process ends at step 1810.

The process for manufacturing the pre-hydrated anhydrous LiOH may also include a step for filling the LiOH (Filled Extruded Netting (or PTFE fiber) Option). The filling step includes a porous membrane (e.g. PTFE membrane) being laminated to the surface of extruded netting (e.g., Naltex® made by Delstar Technologies; thickness ranging from 0.006-0.200 inches, openings as small as 200 micron and as large as 2.5 inches). Openings are filled with anhydrous LiOH powder. Alternatively, the openings may be filled with pre-hydrated LiOH powder and the spraying step below may be skipped. Alternatively, a PTFE fiber may be filled with LiOH powder, as done using the process outlined in U.S. Pat. No. 5,165,399 to Hochberg, which is herein incorporated by reference.

After filling, the sheet is sprayed with water. The spray system may include an ultrasonic spray head that distributes a fine mist of water across the width of the material. The water lay-down flow may be held constant and a line speed controller controls the sheet velocity. The sheet velocity may be determined by a number of parameters or combination thereof, including the starting moisture content, the target moisture content, the sheet weight in mass LiOH/area and the water lay-down flow. A second layer of porous membrane is laminated to the top surface of sheet in order to encapsulate the LiOH powder.

The sheet may be wound onto a cylinder or used as panels. Extruded netting may be used as a spacer between layers of filled sheet in order to provide flow paths between layers of filled sheet. This configuration provides a pore structure between particles and correspondingly results in LiOH adsorbent density that is lower than that of standard LiOH granules. The process 1800b ends at step 1810.

In addition to pre-hydrating LiOH using spraying, pre-hydrating may be performed by using water vapor. By bubbling nitrogen or other CO2 free gas, a 30-33 percent water content by weight may be achieved in one to two hours. Higher water contents may be achieved with increased exposure time. Increasing temperature is expected to reduce this vapor hydration time. Additionally, small water hydration levels of less than five or ten percent may be achieved with exposure to water vapor for less than five minutes.

Figure 19:
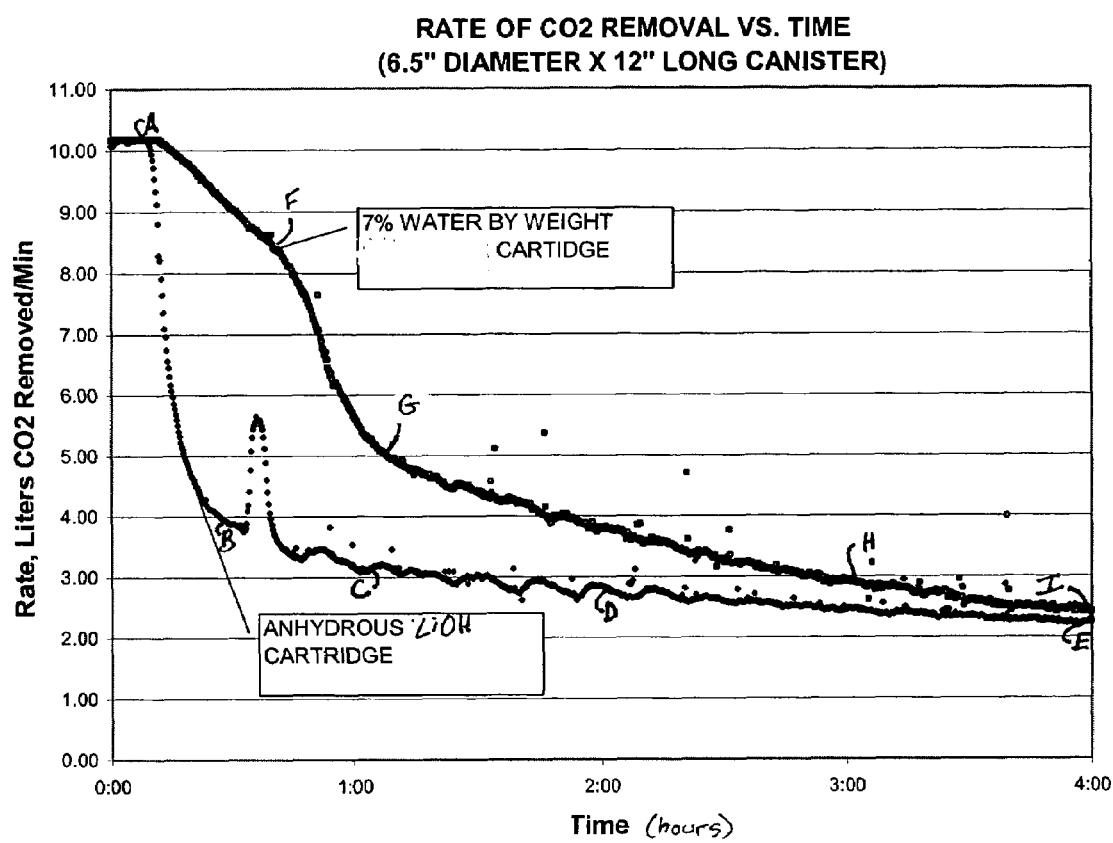
FIG. 19 is a graph of CO2 removal rates for an exemplary anhydrous LiOH sheet or cartridge and a pre-hydrated sheet.

FIG. 19 is a graph of CO2 removal rates for an exemplary anhydrous LiOH adsorbent in sheet form wound into a cartridge, and a pre-hydrated LiOH adsorbent in sheet from, wound into a cartridge. The anhydrous LiOH sheet is enclosed in a canister having dimensions of 6.5 inches in diameter and 12 inches long. The rate of removal of CO2 for the anhydrous LiOH cartridge starts at removing above ten liters per minute of CO2, but after 15 minutes (point A), the CO2 rate of removal drops off sharply to four liters per minute at approximately 30 minutes (point B). At approximately one hour (point C), the removal rate of CO2 is approximately three liters per minute and remains at that rate until approximately two hours (point D). After four hours (point E), the rate of removal of CO2 levels out to about 2.25 liters per minute.

A pre-hydrated LiOH cartridge of seven percent (7%) water by weight having the same dimensions as the anhydrous LiOH cartridge is shown to also start the rate of removal of CO2 above ten liters per minute. However, rather than abruptly dropping off at 15 minutes, the CO2 rate of removal substantially linearly drops off to 8.5 liters per minute at approximately 45 minutes (point F) into the CO2 removal process. A steeper removal rate drop-off begins at approximately 45 minutes (point F) and reaches five liters per minute just after an hour (point G). At that point, the slope decreases and at three hours (point H), the rate of removal of CO2 of the pre-hydrated LiOH sheet is approximately two hours later than that of the anhydrous LiOH cartridge. At approximately four hours (point I), the rate of removal of CO2 is about 2.5 liters per minute, slightly above that of the anhydrous LiOH sheet.

Overall, the comparison between the curves in FIG. 19 shows that the pre-hydrated LiOH cartridge maintains higher CO2 removal rates than the anhydrous LiOH cartridge and for longer durations. Higher and longer CO2 removal rates may be shown by using different pre-hydrated LiOH compounds (e.g., higher or lower density) and having different hydration levels (e.g., higher hydration levels).

Pre-Hydration and Heat Generation

Hydration results in a temperature increase of the LiOH as described by Eqns (1)-(3). After the hydration process, the LiOH adsorbent is allowed to cool. Reducing the amount of anhydrous LiOH in the adsorbent reduces the amount of heat generated during use. Conversely, increasing the amount of LiOH increases the amount of heat generated during use.

A case where there is no heat generation in use (i.e., no temperature increase) is obtained by matching the amount of heat generated in Eqn. (1) with the amount of heat needed in Eqn. (2) describing the LiOH reaction with CO2. Using the heats of reaction listed for the two reaction steps indicates that 36 percent water by weight (mass water/wetted mass) results in zero net heat generation during use. The stoichiometric amount of LiOH hydration occurs with approximately 43 percent water by weight. Between 36 and 43 percent pre-hydration, the system becomes endothermic, which reduces system temperature. Pre-hydration above 43 percent is generally undesirable since the solid LiOH begins to dissolve at such hydration levels, thereby causing the cartridge to lose its solid form and properties.

Other Attributes of Pre-Hydrated LiOH Operation

Figure 20:
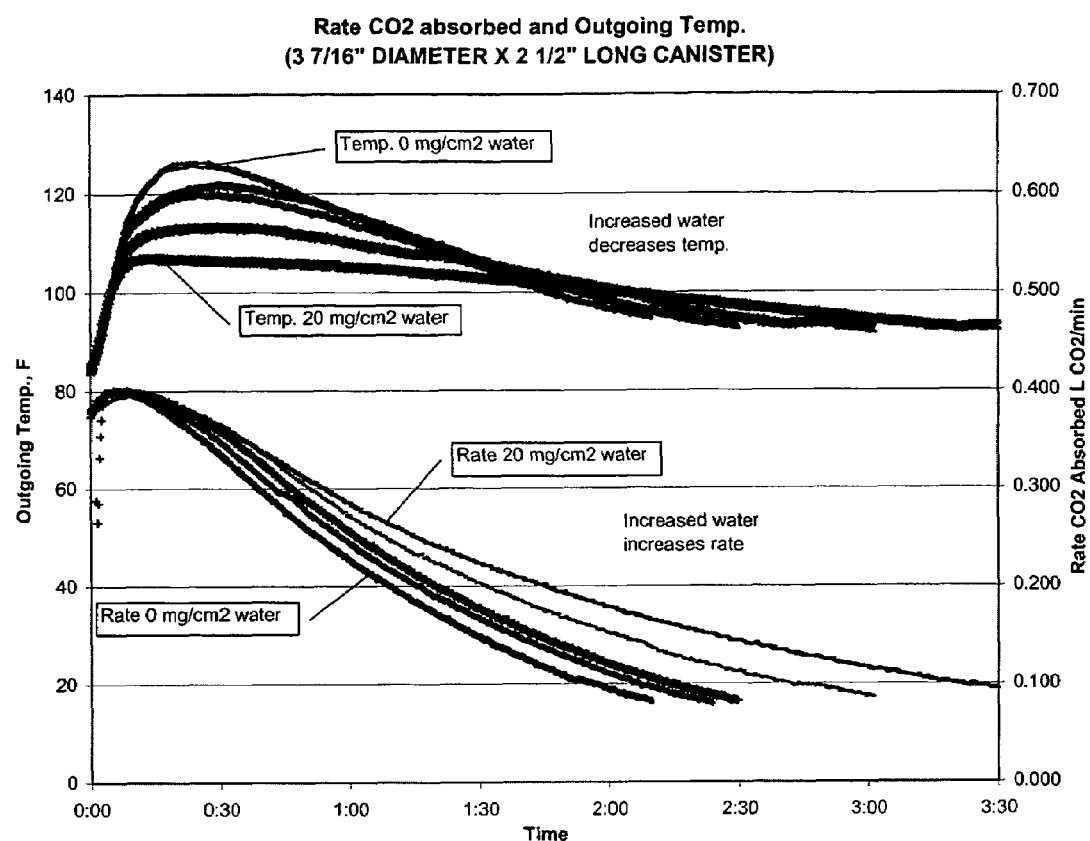
FIG. 20 is a graph of multiple CO2 adsorbent cartridges composed of anhydrous LiOH having different levels of pre-hydration.

FIG. 20 is a graph of multiple CO2 adsorbent cartridges composed of anhydrous LiOH having different levels of pre-hydration. The canister for enclosing CO2 adsorbent cartridges is sized at 3 7/16 inches in diameter and 2.5 inches in length. The CO2 adsorbent cartridges were pre-hydrated with various levels of water; 0, 1.9, 4.7, 9 and 16.5 percent by weight. By pre-hydrating at these levels, results may be viewed on the graph for comparison purposes. As indicated above, increased levels of pre-hydration results in reduced exhaust temperatures. Increasing the pre-hydration level also results in increased CO2 removal rate. This provides a longer duration where CO2 removal rates are to be maintained above minimum levels.

Figure 21:
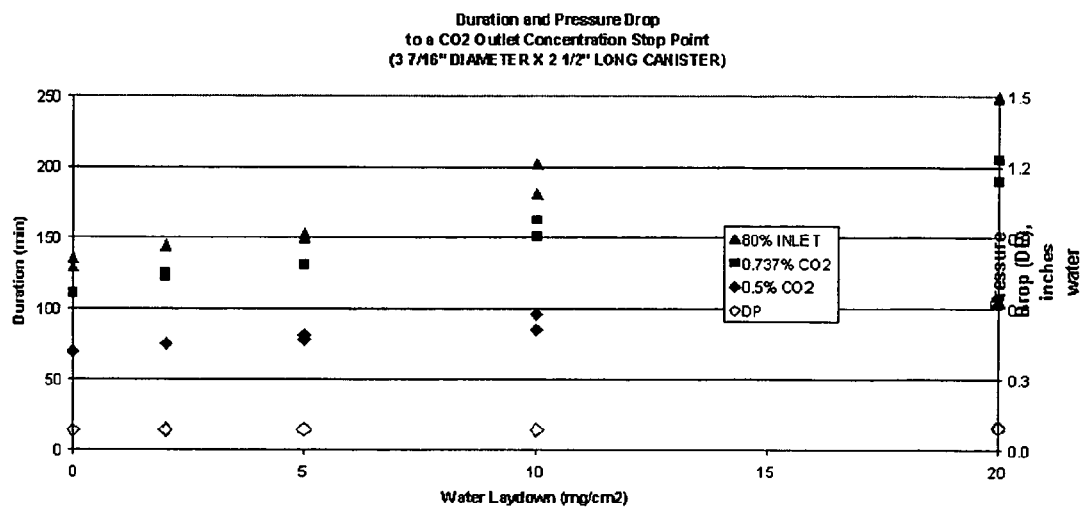
FIG. 21 is a graph of exemplary CO2 adsorbent cartridges for showing CO2 duration times for replacement points.
Figure 22:
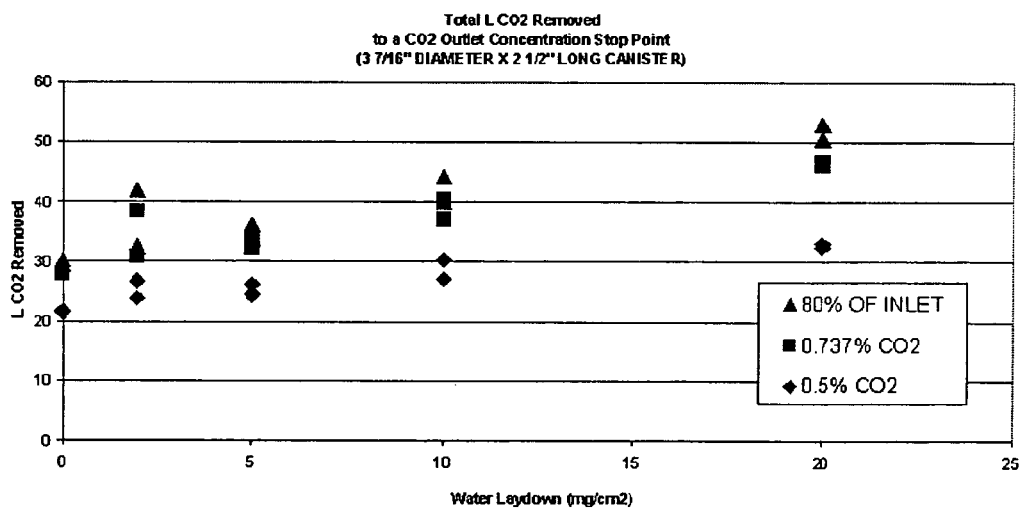
FIG. 22 shows the total CO2 removed upon reaching a replacement point.

FIG. 21 is a graph of exemplary CO2 adsorbent cartridges for showing CO2 duration times for replacement points at 0.5, 0.737 and 0.8 percent CO2. The replacement points are defined by various military and civilian specifications for replacing CO2 adsorbent cartridges to ensure safe CO2 levels, as understood in the art. FIG. 22 shows the total CO2 removed upon reaching a replacement point. In each case, increasing pre-hydration of the LiOH sheet increases the duration and total CO2 removal. The increased CO2 removal rate for the pre-hydrated sheet is in contrast to the results of pre-hydrated or high humidity use of porous granules. Additionally, the pressure drop between the hydrated and non-hydrated samples was not significantly different.

Pre-Hydration Levels Determined by System Requirements

There are a number of different SCBA and scrubber systems that pre-hydrated LiOH in which is effective for removing CO2. These systems, however, may vary widely in their function, operation, and dynamics. For example, an emergency rescue system may be used in stressful situations and be used in high temperature environments for short durations (e.g., 15 minutes) versus a SCUBA system that may be used in low stress situations and be used in cold temperature environments for medium periods of time (e.g., 1-2 hours). The emergency rescue system, therefore, is to be configured as a light weight, minimal heat producing CO2 removal system and the SCUBA system may be configured to be heavier, produce more heat, and last longer than the CO2 removal system for the emergency rescue system. Other types of systems, such as scrubber systems, may have different requirements, such as more relaxed temperature and weight requirements. TABLE I is a chart that offers exemplary configuration guidelines for CO2 removal systems based on specific system applications. It should be understood that the configurations may vary depending on specific system specifications and operating requirements.

CO2 adsorbent systems have a wide range of design requirements, including, but not limited to, pressure drop, CO2 inlet and outlet concentration, total flow, inlet and outlet temperature, duration and total CO2 removal. Thus, a single design does not work for all CO2 adsorbent systems. The required amount of heat generation, desired breathing temperature, required CO2 removal rate, required CO2 removal capacity combine with canister dimensional requirements to determine the amount of pre-hydration desired and the configuration of the anhydrous LiOH adsorbent structure. Other operating parameters, including pressure drop, CO2 removal rate, and CO2 removal capacity, may be adjusted by selection of rib height, rib width, rib spacing, base sheet thickness and oil content/porosity, if using a LiOH sheet in the CO2 removal system. The cartridge canister dimensions and cartridge weight requirements may be used to determine the overall cartridge dimensions.

TABLE I

Pre-Hydration Guidelines
Pre-hydration guidelines

| CO2 Scrubbing Equipment | SCBA (Self Contained Breathing Apparatus) | | Medical Oxygen Extension | SCUBA | Space Suit | Space Shuttle | Navy Sub | Navy Sub | On-Site Air | Industrial CO2 scrubber | Industrial CO2 scrubber |
|---|---|---|---|---|---|---|---|---|---|---|---|
| Human interface | Hood | Hood Hood | Mouth | Mouth | Suit | Cabin | Cabin | Cabin | Room | equipment box | equipment box |
| Air Flow Created by: | Human Lung | Fan | Passive: Thermal | Human Lung | Human Lung | Fan | Fan | Fan | Passive: Thermal | Passive: Thermal | fan | fan |

TABLE I-continued

Pre-Hydration Guidelines
Pre-hydration guidelines

| CO2 Scrubbing Equipment | SCBA (Self Contained Breathing Apparatus) | | Medical Oxygen Extension | SCUBA | Space Suit | Space Shuttle | Navy Sub | Navy Sub | On-Site Air | Industrial CO2 scrubber | Industrial CO2 scrubber |
|---|---|---|---|---|---|---|---|---|---|---|---|
| CO2 Removal rate | High | High High | Low | High | High | High | High | High | High | Low | low |
| Temperature | Low | High High | Neutral | Low | Neutral | Neutral | Moderate | Low | Moderate | Moderate | high |
| Humidity Level | High | High High | High | High | Neutral | Neutral | High | High | Low | Low | Low |
| Pre-Hydration Level | Low-Moderate | Moderate-High | Low | Moderate-High | Low-Moderate | Moderate | Moderate | Moderate | None | Low | Low | Moderate-High |

Pre-Hydration Guideline Legend:
None = <1.0% water
Low = 1.0-10% water
Moderate = 10-20% water
High = 20-43% water For the above pre-hydration guidelines, pre-hydration guideline legend provides exemplary pre-hydration levels. However, is should be understood that these levels are approximate and that the levels in TABLE I may be changed as the system requirements and conditions of use (e.g., environment) change.

In general, a high CO2 removal rate favors pre-hydration, except in cold temperatures. A high temperature favors high pre-hydration. A low humidity level favors high pre-hydration for warm temperatures, and low pre-hydration for cold temperatures. Note: Passive absorption applications often need the extra heat of hydration to maintain higher adsorbent temperatures, and therefore, even in warm environments, high humidity, and high CO2 removal rates, a low pre-hydration level may be chosen.

Two exemplary LiOH cartridges are provided below. These LiOH cartridges are configured for specific CO2 removal systems to operate in certain operating conditions.

EXAMPLE 1

A pre-hydrated LiOH adsorbent sheet, wound into a cartridge may be made from the following components by spraying water onto the ribbed side of the sheet surface in order to achieve a 7% w/w water content:
LiOH adsorbent density 0.71 g/cm$^3$, 2.5 percent polyethylene, 0.025 inch rib height, 0.060 inch rib width, 0.120 inch channel width, 0.070 inch sheet thickness, density before water 134 g/ft$^2$, cartridge length 12 inches, cartridge diameter 6½", wound on a ½" diameter polyethylene core with core plug.

EXAMPLE 2

LiOH CO2 cartridges may be made from the following components by spraying water onto the ribbed side of the sheet surface at the following levels: 0, 1.9, 4.7, 9 and 16.5 percent water weight/wet weight:
LiOH adsorbent density between 0.59 and 0.66 g/cm$^3$, 2.5 percent polyethylene, 0.032 inch rib height, 0.060 inch rib width, 0.120 inch channel width, 0.050 inch sheet thickness, density before water 94 g/ft$^2$, cartridge length 2.5 inch, cartridge diameter 3$\frac{7}{16}$ inches, wound on a ½ inch diameter polyethylene core with core plug.

The adsorbent LiOH density for Example 1 is 0.71 g/cm$^3$. The LiOH adsorbent density for Example 2 is 0.59 to 0.66 g/cm$^3$. The LiOH adsorbent density in sheet form for a U.S. Navy sub application is typically 0.81 g/cm$^3$. The LiOH adsorbent density for CO2 adsorbent (sheet) according to the principles of the present invention may be controlled by the amount of oil used at the extrusion step. Removal of the oil at the extraction step results in voids between the LiOH powder particles that are within the adsorbent sheet. Thus, higher oil levels result in higher void levels within the sheet and subsequently lower LiOH adsorbent density. Utilizing this density varying process, LiOH adsorbent density may be produced as low as 0.54 g/cm$^3$ and as high as approximately 0.85 g/cm$^3$. Attaining adsorbent LiOH densities outside of this range is achievable.

The innovative concepts described in the present application can be modified and varied over a wide rage of applications. Accordingly, the scope of patented subject matter should not be limited to any of the specific exemplary teachings discussed, but is instead defined by the following claims.

We claim:

1. A CO2 removal system, comprising:
   a member having a first opening and a second opening to enable air flow containing carbon dioxide (CO2) to pass from the first opening to the second opening; and
   lithium hydroxide (LiOH) adsorbent supported by said member and having an initial water content above an anhydrous level, wherein the density of the LiOH adsorbent is less than approximately 1.0 g/cm$^3$.

2. The system according to claim 1, wherein the LiOH is configured as granules.

3. The system according to claim 1, wherein said member is configured in at least one sheet.

4. The system according to claim 3, wherein the at least one sheet has a first side and a second side, at least one side including a plurality of protrusions.

5. The system according to claim 4, wherein the initial water content is initially absorbed in a side of the sheet with protrusions.

6. The system according to claim 3, wherein the at least one sheet is configured as a cartridge.

7. The system according to claim 1, wherein said member is a canister, and wherein air is directed to flow through the canister.

8. The system according to claim 1, wherein the initial water content of said LiOH adsorbent is between the anhydrous level and approximately 10 percent by weight.

9. The system according to claim 1, wherein the initial water content of said LiOH adsorbent is between approximately 10 percent and approximately 20 percent by weight.

10. The system according to claim 1, wherein the initial water content of said LiOH adsorbent is between approximately 20 percent and approximately 43 percent by weight.

11. The system according to claim 1, wherein the initial water content of the LiOH is between approximately 36 and approximately 43 percent by weight.

12. The system according to claim 1, wherein the initial water content of said LiOH adsorbent is between the anhydrous level and approximately 43 percent by weight.

13. The system according to claim 1, wherein the $CO_2$ removal system is a self-contained breathing apparatus.

14. The system according to claim 13, wherein the self-contained breathing apparatus is configured as an underwater breathing apparatus.

15. The system according to claim 13, wherein the self-contained breathing apparatus is adapted to be used in a medical apparatus.

16. The system according to claim 13, wherein the self-contained breathing apparatus is adapted to be used in a first responder apparatus.

17. The system according to claim 13, wherein the self-contained breathing apparatus is adapted to be used in a fire fighting apparatus.

18. The system according to claim 13, wherein the self-contained breathing apparatus is adapted to be used in a chemical, biological, radiological, and nuclear (CBRN) apparatus.

19. The system according to claim 13, wherein the self-contained breathing apparatus is adapted to be used in a space suit.

20. The system according to claim 1, wherein the $CO_2$ removal system is a scrubber system.

21. The system according to claim 1, further comprising a head cover.

22. The system according to claim 1, further comprising a mouthpiece.

23. The system according to claim 1, wherein said LiOH adsorbent is in the form of a powder enclosed in non-woven sheets of material.

24. The system according to claim 23, wherein the material is gas permeable.

25. An article, comprising:
a lithium hydroxide (LiOH) adsorbent for removing $CO_2$, and having an initial water content above an anhydrous level, wherein the density of said LiOH adsorbent is less than approximately 1.0 $g/cm^3$.

26. The article according to claim 25, wherein the initial water content of said LiOH adsorbent is between the anhydrous level and approximately 10 percent by weight.

27. The article according to claim 25, wherein the initial water content of said LiOH adsorbent is between approximately 10 percent and approximately 20 percent by weight.

28. The article according to claim 25, wherein the initial water content of said LiOH adsorbent is between approximately 20 percent and approximately 43 percent by weight.

29. The article according to claim 25, wherein the initial water content of said LiOH adsorbent is between approximately 36 percent and approximately 43 percent by weight.

30. The article according to claim 25, wherein the initial water content of said LiOH adsorbent is less than approximately 43 percent by weight.

31. The article according to claim 25, further comprising a gas permeable material that encloses said LiOH adsorbent.

32. The article according to claim 25, wherein said LiOH adsorbent is in the form of granules.

33. The article according to claim 32, further comprising a canister in which said LiOH adsorbent is contained.

34. The article according to claim 25, wherein said LiOH adsorbent is configured in a sheet composing a polymer.

35. The article according to claim 34, wherein the sheet includes a first side and a second side, at least one side having structural protrusions.

36. The article according to claim 25, wherein said LiOH adsorbent includes a polymer.

* * * * *